US010548562B2

(12) United States Patent
Hoppmann et al.

(10) Patent No.: US 10,548,562 B2
(45) Date of Patent: Feb. 4, 2020

(54) STETHOSCOPE WITH EXTENDED DETECTION RANGE

(71) Applicants: University of South Carolina, Columbia, SC (US); New Mexico Institute of Mining and Technology, Socorro, NM (US)

(72) Inventors: Richard Hoppmann, Columbia, SC (US); Toufic Robert Haddad, Columbia, SC (US); Keith Reeves Barron, Jr., Columbia, SC (US); Andrei Zagrai, Socorro, NM (US)

(73) Assignees: UNIVERSITY OF SOUTH CAROLINA, Columbia, SC (US); NEW MEXICO INSTITUTE OF MINING AND TECHNOLOGY, Socorro, NM (US)

(*) Notice: Subject to any disclaimer, the term of this patent is extended or adjusted under 35 U.S.C. 154(b) by 0 days.

(21) Appl. No.: 15/979,529

(22) Filed: May 15, 2018

(65) Prior Publication Data

US 2018/0325487 A1 Nov. 15, 2018

Related U.S. Application Data

(60) Provisional application No. 62/506,025, filed on May 15, 2017.

(51) Int. Cl.
*A61B 7/04* (2006.01)
*A61B 7/02* (2006.01)
*A61B 8/00* (2006.01)
*A61B 8/08* (2006.01)
*G06F 3/16* (2006.01)
*H04R 1/46* (2006.01)

(52) U.S. Cl.
CPC ............ *A61B 7/04* (2013.01); *A61B 7/026* (2013.01); *A61B 8/4488* (2013.01); *A61B 8/461* (2013.01); *A61B 8/5223* (2013.01); *A61B 8/5246* (2013.01); *A61B 8/5261* (2013.01); *A61B 8/56* (2013.01); *G06F 3/165* (2013.01); *H04R 1/46* (2013.01)

(58) Field of Classification Search
CPC ......... A61B 7/04; A61B 7/026; A61B 8/4488; A61B 8/461; A61B 8/5223; A61B 8/5246; A61B 8/5261; A61B 8/561; A61B 8/56; G06F 3/165; H04R 1/46
USPC .......................................................... 381/67
See application file for complete search history.

(56) References Cited

U.S. PATENT DOCUMENTS

| 5,492,129 A * | 2/1996 | Greenberger ............ A61B 7/04 181/131 |
| 6,512,830 B1 * | 1/2003 | Orten ....................... A61B 7/04 381/67 |
| 2018/0317789 A1 * | 11/2018 | Ransbury ............ A61B 5/02438 |

* cited by examiner

*Primary Examiner* — Vivian C Chin
*Assistant Examiner* — Douglas J Suthers
(74) *Attorney, Agent, or Firm* — Burr & Forman LLP; Douglas L. Lineberry

(57) ABSTRACT

An improved stethoscope design with an extended detection range for sounds above and below the range of human hearing and artificial intelligence connection to other clinical data for analysis, wherein the stethoscope assesses spatial distribution of bodily sounds using a sensor array as well as amplifies the volume of bodily sounds and provides for recording, receiving and processing same.

15 Claims, 6 Drawing Sheets

STETHOSCOPE WITH EXTENDED DETECTION RANGE

BACKGROUND OF THE INVENTION

1) Field of the Invention

The present invention relates to an improved stethoscope design with an extended detection range, extended frequency bandwidth, which may be used with an artificial intelligence connection to other clinical data for analysis.

2) Description of Related Art

The human ability to sense sound is the result of an approximately four billion year evolutionary cycle. Hearing enables a listener to hear/perceive natural sounds that exist in the environment, which aids with locating food, as well as helps the listener avoid becoming food. The human ear responds to disturbances/temporal variations in pressure and is very sensitive. The ear has: more than six (6) orders of magnitude in dynamic range of pressure sensitivity; twelve (12) orders of magnitude in sound intensity; and three (3) orders of magnitude in frequency (20 Hz-20 KHz). Further, having two ears greatly enhances 3-D localization of sounds, and also the determination of pitch (i.e. frequency resolution). This may extend into the megahertz range as well.

As social animals, human hearing has developed to improve detection of human-made sounds. Social animals are primarily interested in their own species, and, hence, humans are primarily interested in hearing human-made sounds produced by voices. The frequency range of sounds produced by voices—the totality of the physics associated with air as a medium plus vibrating vocal chords in our larynx/voice box plus hyoid bone plus acoustic cavities of our lungs plus throat plus mouth plus nasal passage/sinus cavity dictates what the acoustic power spectrum of the human voice can/cannot be. Over the course of time, hearing co-evolved with the sounds that voices make. Further, human hearing has evolved to possess a limited range in order to avoid hypersensitivity to sounds, such as, for example, infra-sound (f<20 Hz). It would be significantly detrimental if human hearing was constantly being "masked" by hearing draft/wind noises as one walked or ran.

One particular use of human hearing is to diagnose health by listening to noises made by the human body, such as by use of a stethoscope. Stethoscopes date back to Rene Laennec, a personal physician of Napoleon, who invented the stethoscope in 1815. That device picked up acoustic vibrations, such as heart and breathing sounds from the body surface and transmitted them via a conductive, air-filled medium, which is typically a pipe or a rubber hose. This style of stethoscope remains in use today because of its simplicity and robustness. For over 200 years the stethoscope has been used by healthcare providers to listen to a variety of body systems such as the heart, lungs, blood vessels, and gastrointestinal tract for sounds that aid in the diagnosis and clinical management of patients.

A typical stethoscope consists of a diaphragm or bell that is placed on the body surface of the patient and tubing that transmits the body sounds to the examiner's ears for interpretation. Only sounds loud enough and within the frequency of the hearing range of the listener can be heard and interpreted for assessing the health of the patient. More recently, electronic stethoscopes have been introduced that can amplify body sounds and also record and graphically display the frequency of the sounds in real time. However, to date, only frequencies within the human hearing range have been systematically evaluated.

It has been reported that healthcare practitioners experience difficulties listening and identifying heart sounds with a stethoscope, especially in a working medical facility filled with a plethora of background noise. Accordingly, it is an object of the present disclosure to assist in learning and accurately identifying heart and other body sounds, as well as new sounds that will help with patient diagnosis and medical treatment. What is needed in the art is an improved stethoscope design. Information from the stethoscope of the current disclosure may be used in combination with other patient data and assessed by artificial intelligence and deep learning to enhance the accuracy of diagnoses and create a personalized patient profile. The device can be used in medical research to assess the effectiveness of treatment such as that of new medications since it will be able to provide earlier and more sensitive detection of progression or regression of disease. This extended analysis of body sounds can also be used as an educational tool in the health sciences.

SUMMARY OF THE INVENTION

The above objectives are accomplished according to the present invention by providing in a first embodiment, a method for monitoring and analyzing body sounds. The method includes placing at least one detection device in contact with a body to be monitored, detecting body sounds within, above and below a frequency range of human hearing, assessing spatial distribution of sounds using an array of sensors in the detection device, amplifying the volume of body sounds via the detection device, recording the body sounds in at least one body location; and receiving and processing the body sounds to determine a state of health. Further, the method includes a baseline sound recording for a body based on the body sounds recorded. This may act as the "normal" reading for a patient or animal, even if they are in a healthy, diseased or injured state. Still further, the method comprises taking additional body sound recordings over time. Still yet further, the method compares the body sound recordings taken at different times to the baseline recording to determine differences in the body sound recordings. Further yet, the method analyzes at least one of frequency, intensity, wave form, nonlinearity of waveform, or location of sound detected in a physiological cycle. Still further, the method combines results from the analysis with other health data points of the body being monitored. Still even further, the method analyzes the combined results by deep learning and artificial intelligence to provide earlier and more accurate diagnoses. Furthermore, a second detection device is placed on the body being monitored at a location separate from the at least one detection device. Even further, the method analyzes nonlinearity of the body sounds and associates same with a health status of the body.

In an alternative embodiment, a system is provided for analyzing sounds generated by an animal's body. The system includes: at least one detection device for auscultation of internal sounds from the animal's body wherein the auscultated sounds are within, above and below human hearing range; the detection device is in wireless communication with a receiver, which receives the auscultated internal sounds from the detection device; a processor, in communication with the receiver, generates audio and video output formed from the internal sounds auscultated by the detection device; and a monitor for displaying the audio and video output from the processor. Further, the system communicates with at least one communication system other than the monitor. Still further, the detection device has an offset peripheral margin that may contain an adhesive to affix the recording disk to the body surface to improve quality of recording of the body sounds and decrease external noise. Further still, the system forms a baseline sound recording for a body based on the body sounds recorded. Even further, the system analyzes at least one aspect of the body sounds such as frequency, intensity, wave form, nonlinearity of waveform, or location of sound detected in a physiological cycle. Further yet still, a second detection device may be placed on the animal's body being monitored at a location separate from the at least one detection device. Even further still, system analyzes nonlinearity of the body sounds and associating same with a health status of the body.

In a still further embodiment, device for monitoring and analyzing body sounds is provided. The device includes a sound detection apparatus for detecting sounds within, above and below a human range of hearing; an amplifier for amplifying the detected sounds; at least one volume control; a transmitter for transmitting the sounds; a first surface for contacting a body, the first surface defining an offset peripheral margin; a record button to initiate or cease recording of the body sounds; and a power indicator.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

Figure 1:
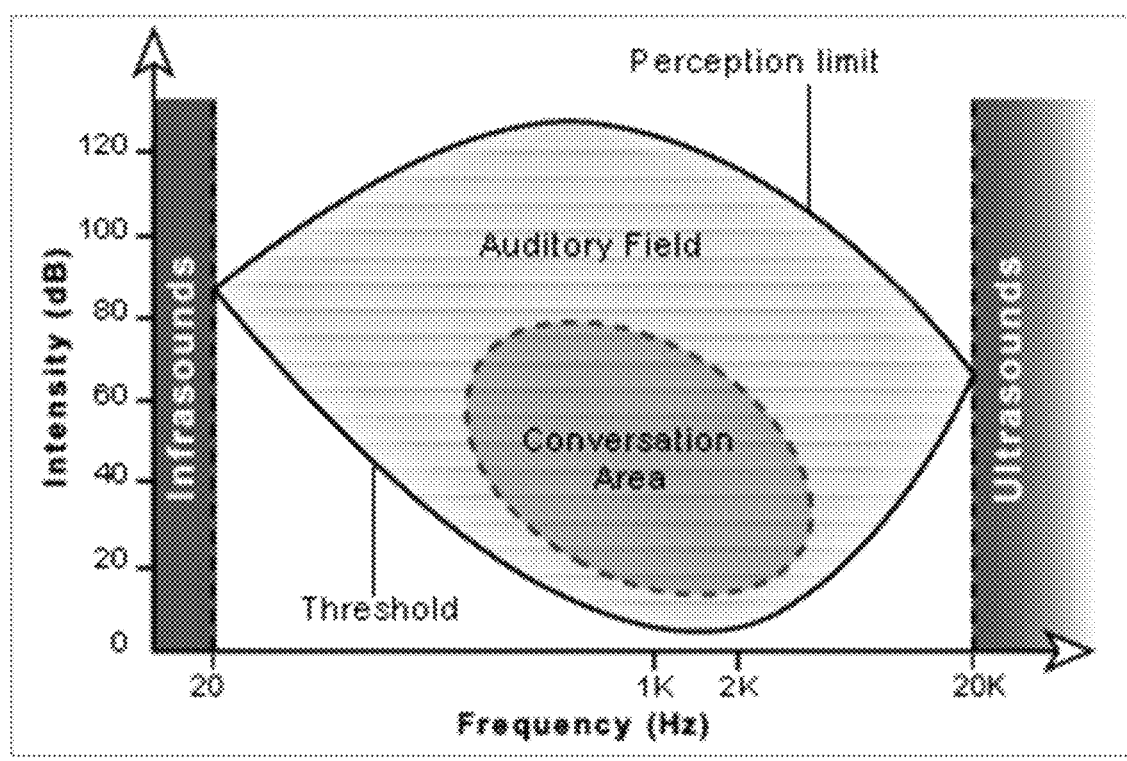
FIG. 1 shows an audiometric curve which displays the range of sounds that humans can hear.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The present invention will amplify body sounds and also expand the range of sounds detected to above and below the frequency range of human hearing, approximately 20 Hz to 20,000 Hz. For instance, infrasound below 20 Hz may be detected, as well as ultrasound above 20,000 Hz. For instance, infrasound may be detected as low as 1 Hz and ultrasounds detected at the 30,000, 40,000, 50,000, 60,000, 70,000 or higher levels, including midpoints between same such as 32,000 Hz, 43,000 Hz, 57,000, 66,000 Hz or ranges of same such as from 1 Hz to 50,000 Hz, 3 Hz to 67,000 Hz, 2 Hz to 80,000 Hz, etc. In one aspect, the current disclosure may provide an improved stethoscope for auscultation or listening to the internal sounds of an animal or human body. The current disclosure will also detect sounds within the human range of hearing.

FIG. 1 displays an audiometric curve that shows the range of sounds that humans can hear, with frequency on the x-axis and sound level or intensity on the y-axis. The hearing of many individuals has been summarized to show the sounds that humans with normal hearing are able to hear (light gray area), in the context of where human speech falls (dark gray area).

Figure 2:
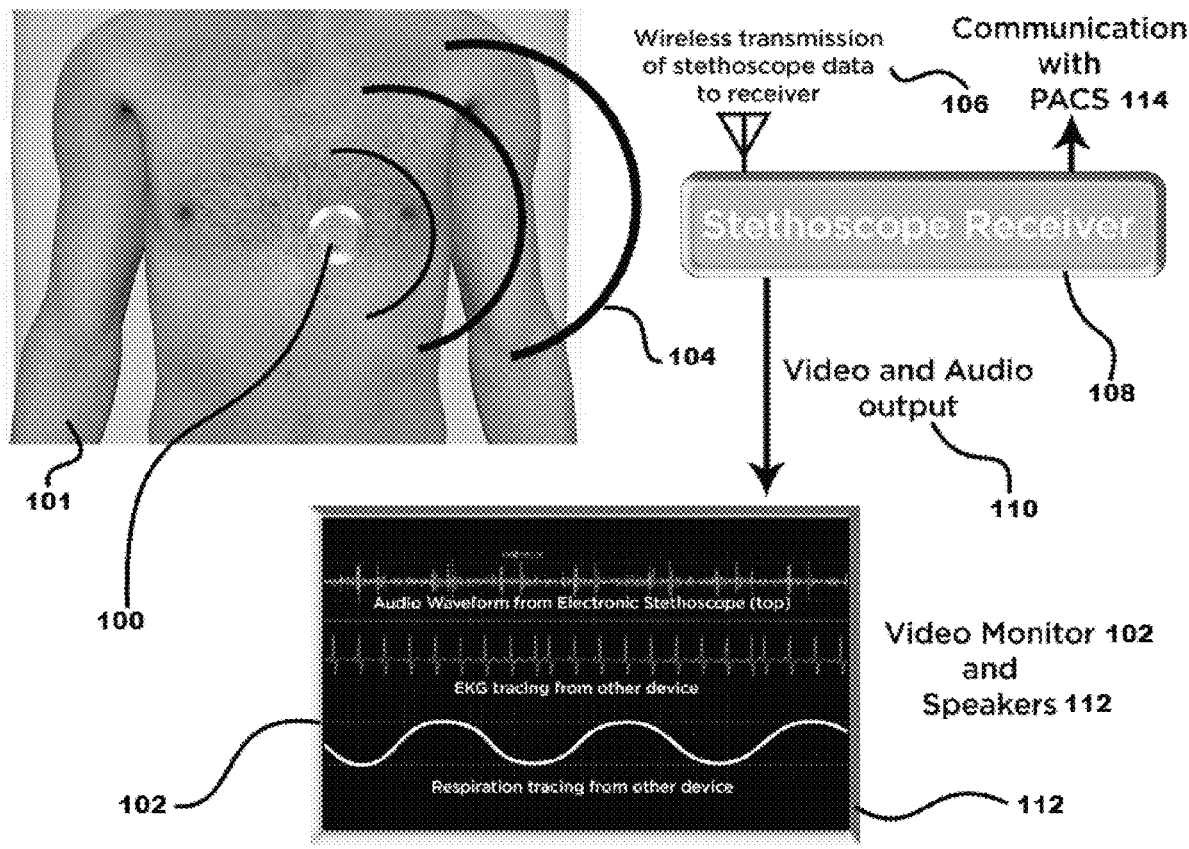
FIG. 2 shows a system employing a recording device and monitor of the current disclosure.

FIG. 2 shows one embodiment of detector 100, which in one embodiment may be an electronic stethoscope, of the present disclosure on a patient 101. Detector 100 may comprise an amplifier for boosting electric current to provide a much-magnified version of the original sound (the sounds generated from the patient's body). Detector 100 may receive and amplify sounds generated by a patient, such as a human or other mammal or animal. A monitor 102 will display all frequencies detected by detector 100 as well as the sound wave form and intensity (loudness) 104 of each sound. The detected aspects include, but are not limited to, frequency, wavelength, amplitude, nonlinearity of waveform, intensity, pitch and tone of the received sound. All of these various aspects of a sound help give each sound a unique pattern. Further, this uniqueness will exist between different patients. Thus, listening to Mr. Smith's heart will generate a different sound than that generated by Ms. Johnson's heart, even if both have healthy hearts with no signs of disease. These sonic differences are used as part of the present disclosure to form a sonic "fingerprint" for a patient that aids in treatment, such as diagnostic interpretation of the sounds, as well as helps distinguish one patient from another based on the individual aspects of the sounds each patient naturally produces.

Transmission of the sound wave form and intensity 104 may be via wireless communication 106 from monitor 102 to a receiver 108. Such wireless communication may take the form of IR wireless communication, satellite communication, broadcast radio waves, microwave radio, Bluetooth, Zigbee, etc., as known to those of skill in the art. Receiver 108 may provide video and audio output 110 to monitor 102, which may have speakers 112 incorporated into same. Receiver 108 may also comprise a processor 111, as known to those of skill in the art, in communication with receiver 108 for receiving input, analyzing, converting, manipulating, processing, generating output, etc., with respect to the information received by detector 100. In one example, receiver 108 may be a A/V (audio/video) receiver that provides surround-sound capability, digital audio processing, digital video processing and switching, automatic speaker setup systems and network audio and video set-up. Receiver 108 may also communicate with other systems such as a PACS system 114, which stands for Picture Archiving and Communication System, for storage, retrieval, identification, and other manipulations of the data. Monitor 102 may display various information regarding sound wave form and intensity 104, such as the audio wave form, amplitude, etc. Monitor 102 may also receive and display information from other devices such as EKG information and/or respiration, pulse, heart rate, temperature, etc., obtained from other devices and transmitted to monitor 102.

The size of the detector 100 is such as to allow not only for listening to sound at one particular location on a human body, but also for assessing spatial distribution of sound to aid diagnostics. For example, a detector 100 on a patient's chest can be used to determine where within the chest a sound originates. Sound frequency and wave form will be placed in the precise location within the appropriate physiological cycle such as heart sounds in the cardiac cycle or a breath sound in the respiratory cycle. A key feature of the current disclosure is that new sounds either too soft to be heard or with frequencies outside of the normal human hearing range will be identified. These are expected to provide additional information to aid in diagnosis and clinical management of the patient.

In one embodiment, detector 100 may include an audio sound transducer, which may include both: (1) input sensors, which convert sound and body vibration into an electrical signal which may include, but is not limited to a microphone or piezoelectric sensors; and (2) output actuators that convert the electrical signals back into sound such as a loudspeaker. The monitor can display the sound data with other clinical digital input data such as the EKG and respiratory breathing cycle as seen in the example display in 102.

Figure 3A:
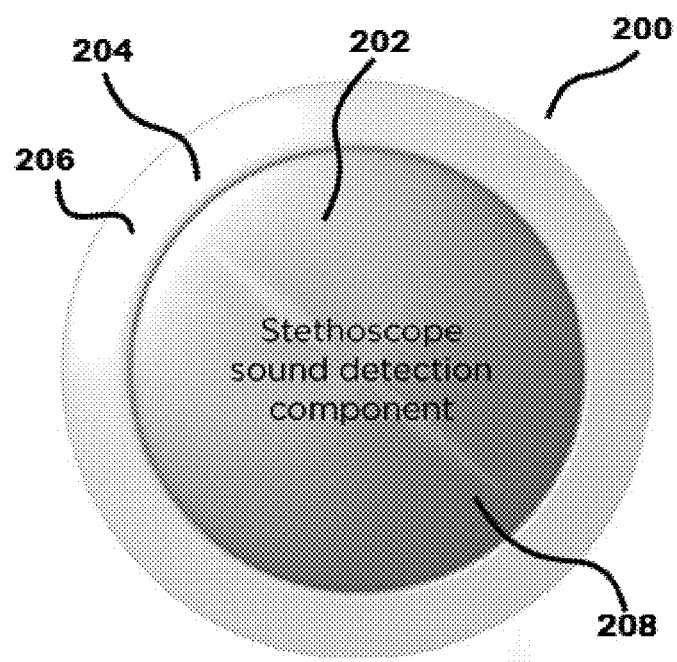
FIG. 3A shows a bottom view of one embodiment of a recording device of the current disclosure.
Figure 3B:
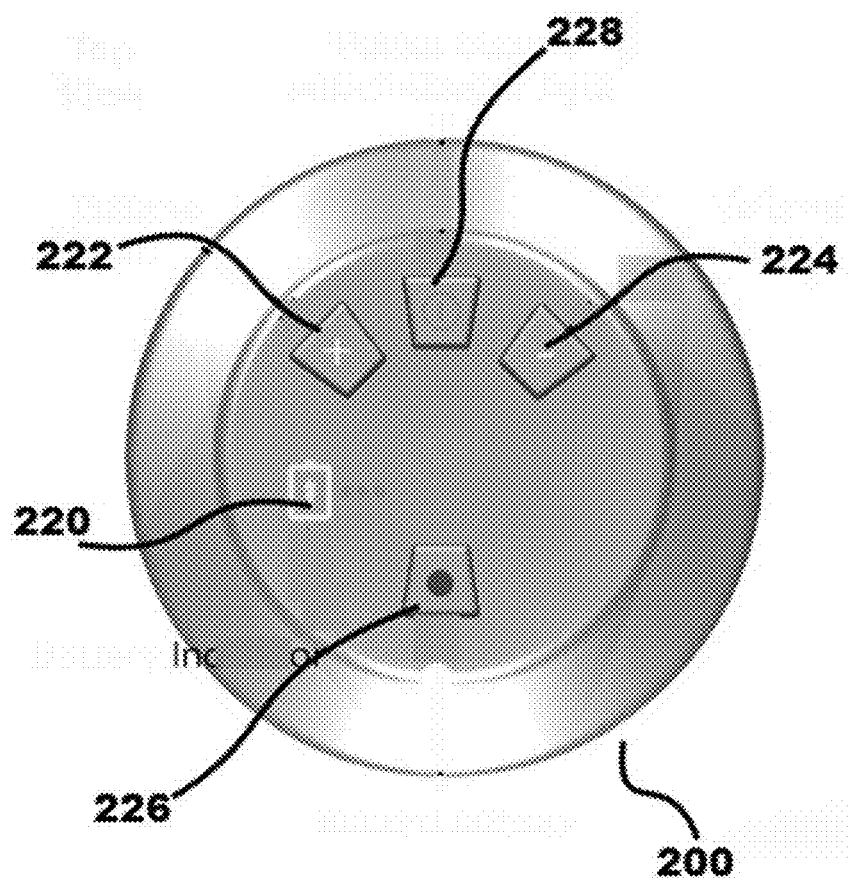
FIG. 3B shows a top view of one embodiment of a recording device of the current disclosure.
Figure 3C:
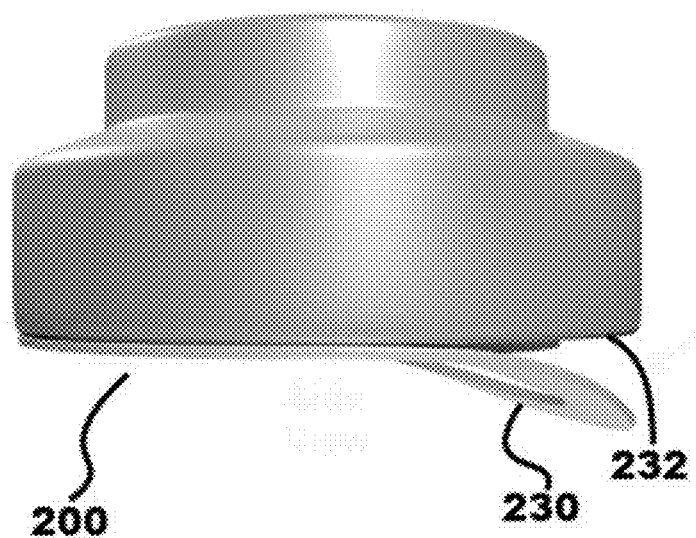
FIG. 3C shows a side view of one embodiment of a recording device of the current disclosure.

FIGS. 3A, 3B, and 3C show one embodiment of a recording device of the current disclosure. FIG. 3A shows a bottom view of a recording device 200 of the current disclosure. Detector disk 202, which in one embodiment may be approximately 5.0 cm in diameter, has an offset 204 at the margin 206 of recording device 200 to allow an adhesive, such as for purposes of example only and not intended to be limiting, double-sided adhesive tape, not shown, to contact the disk and the patient's body surface while allowing the recording portion 208 in the center of detector disk 202 to make continuous fixed contact with the body surface. This will allow maximum quality recording of the body sounds while minimizing or eliminating noise from movement of the disk on the body surface.

FIG. 3B shows a top down view of recording device 200. Device 200 may include a battery indicator 220, volume controls for increasing volume 222 and decreasing volume 224, a record button 226 to initiate or cease recording, and a power indicator 228 to indicate when device 200 is powered on or powered off or the batter is at a certain power level. FIG. 3C shows a side view of recording device 200 showing double-sided adhesive tape 230 affixed to bottom 232 of recording device 200. Tape 230 also helps to create an additional barrier to external noise to further increase the efficiency of recording device 200, as well as improves the quality of recording of the body sounds.

Recording and archiving the data received by device 200, as known to those of skill in the art, can serve as a baseline against which changes in the sounds can be assessed for each individual. In addition, this extended analysis of body sounds both below and above the range of human hearing, can provide new data that can be combined with other important clinical data of the patient such as an electrocardiogram, pulmonary function test data, ultrasound findings, and blood pressure readings for deep learning and artificial intelligence assessment of the patient's health. This will contribute to more accurate diagnoses and creation of a personal patient profile and allow for the application of "precision" medicine for the individual patient.

One essential element of the current disclosure is a broad frequency acoustic detection device that makes contact with the body surface in the area where the body sound can be heard (over the heart, lungs, etc.). The device will detect and assess spatial distribution of various body sounds and transmit sound data with a wired or wireless connection (i.e. Bluetooth) to a computer/smartphone/other electronic device for visual display, projection of the sound, and recording of the sound data. The sound reception mechanism can range from a traditional vibratory receiver, piezo element audio transducer, contact pin receiver, or other form of acoustic reception device. In one embodiment, a microphone input transducer, a sound transducer that can be classed as a "sound sensor" which produces an electrical analogue output signal which is proportional to the "acoustic" sound wave acting upon its flexible diaphragm, may be used. The microphone would form a signal that is an "electrical image" representing the characteristics of the acoustic waveform. Multiple sensors arranged in the array, e.g. several microphones, will provide information on spatial distribution of sound. Generally, the output signal from a microphone is an analogue signal either in the form of a voltage or current which is proportional to the actual sound wave. The most common types of microphones available as sound transducers are Dynamic, Electret Condenser, Ribbon and the newer Piezo-electric Crystal microphones.

The sound data received by detector 100 or 200 may be permanently recorded as well as transmitted to distant sites in real time for others to view and hear. The detector may be manually pressed to the body or affixed to the body via double-sided adhesive contact tape, or other means as known to those of skill in the art, to stabilize the disk on the body surface. The acoustic receptor device may be a stand-alone device or combined with digital data from other medical detection devices such as those used to detect and record electrocardiograms, pulmonary function tests, body temperature, ultrasound images, or blood oxygenation.

The method of the current disclosure to record and analyze body sounds with frequency reception beyond the normal hearing range is novel in the diagnosis and clinical management of patients. Nonlinear interactions of these sounds may be explored to derive new diagnostic features. A sound wave propagates through a material as a localized pressure change. Nonlinearity of the body sound waveform may be caused by various factors. Examples include non-linearity due to two body surfaces being in contact, which leads to different compressional and extensional cycles effectively modulating the propagating sound pressure waves. In addition, increasing the pressure of a gas or fluid increases its local temperature. The local speed of sound in a compressible material increases with temperature; as a result, the wave travels faster during the high pressure phase of the oscillation than during the lower pressure phase. This affects the wave's frequency structure; for example, in an initially plane sinusoidal wave of a single frequency, the peaks of the wave travel faster than the troughs, and the pulse becomes cumulatively more like a saw tooth wave. In other words, the wave self-distorts. In doing so, other frequency components are introduced, which can be described by the Fourier series or other signal processing methods such as Hilbert Transform. This phenomenon is characteristic of a non-linear system, since a linear acoustic system responds only to the driving frequency. This always occurs but the effects of geometric spreading and of absorption usually overcome the self-distortion, so linear behavior usually prevails and nonlinear acoustic propagation occurs only for very large amplitudes and only near the source. By analyzing nonlinear interactions of sound generated from a patient, new body sounds will likely be discovered that aid in diagnosis and improving patient care. Combining these sounds acquired in a single or multiple locations with other clinical data such as pulmonary function test data and ultrasound images and analyzing with artificial intelligence and deep learning will provide a more comprehensive and unique approach to patient diagnosis and management.

In one embodiment, the current disclosure provides a disk acoustic receiver that will make contact with the body similar to a stethoscope but in addition to detecting body sounds such as heart sounds normally heard with a stethoscope it will also detect sounds above and below the frequency levels of human hearing. Nonlinearity in the signal will be considered as a part of diagnostic features. Nonlinear distortion is a term used in fields such as electronics, audio and telecommunications to describe the phenomenon of a non-linear relationship between the "input" and "output" signals of—for example—an electronic device. The receiver will amplify and detect all body sounds within the specified detection ranges and thereby allow diagnoses to be made earlier and more accurately. Information from the device may also be combined with other health information such as an electrocardiogram (EKG) and pulmonary function testing and analyzed with artificial intelligence to provide a more complete picture of the patient's health resulting in precision medical care. Analysis may be performed by Artificial Intelligence/Machine Learning medical software to analyze the data and propose a diagnosis. Examples may include IBM Watson(https://www.ibm.com/watson/health/), Isabel(https://www.isabelhealthcare.c om/), and Human DX (https://www.humandx.org/).

This device will enhance the ability to detect and assess body sounds both in and outside the normal range of hearing giving a medical manufacturer a definite market advantage. Moreover, researchers and the pharmaceutical industry will have a more accurate, more sensitive, and more cost effective way to conduct research and assess therapeutic and preventive strategies which will be a significant advantage. For those manufacturers engaged in multimodality medical devices combining the device of this disclosure with other medical devices such as ultrasound, electrocardiograms, or pulmonary function testing would give them a definite market advantage. Further, manufacturers of educational tools such as electronic stethoscopes and medical simulators would gain a market advantage using the device of the current disclosure.

Education Applications

Recording and displaying heart sounds in real-time for learners will allow opportunities for instructor directed and self-directed learning of auscultation (listening and interpreting body sounds with a stethoscope). Using artificial intelligence and deep learning interpretation of the heart sounds alone or in combination with other clinical information such as lung sounds, EKG, pulmonary function tests, ultrasound and pulse oxygenation will not only enhance clinical diagnoses but provide instructor directed and self-directed opportunities not presently available. The stethoscope disk and/or the display monitor will have an AI on-off activation switch. Thus, the learner can interpret the data and draw clinical conclusions without AI assistance then activate the AI component and compare results. The comparison can also be analyzed and feedback given to the learner. This would provide tremendous opportunities of directed and self-directed learning that do not presently exist.

For purposes of example only and not intended to be limiting, one can consider the classic pathological heart sound that appears in a patient with chronic hypertension—the fourth heart sound (S4). The S4 sound is due to thickening of the wall of the left ventricle that decreases the compliance of the ventricle to accept blood. This heart sound is heard when the left atrium contracts and attempts to "top off" or squeeze more blood into a non-compliant left ventricle. With persistent hypertension the thickened left ventricular wall and non-compliant ventricle can lead to heart failure. This scenario of hypertension leading to left ventricular thickening (hypertrophy) and heart failure is a very common cause of heart failure across the world.

Amplifying the S4 and identifying additional sounds above and below the normal range of human hearing that to date have gone unappreciated will allow the examiner to detect the development of non-compliance of the left ventricle earlier in the process than would have been possible with a traditional stethoscope. This information could then be used to better manage the patient's hypertension such as initiation or change in blood pressure medications.

Another cardiac example is the development of the third heart sound (S3) which can indicate heart failure. S3 can be caused by a sudden deceleration of blood filling the left ventricle due to left ventricular dysfunction. Having the ability to assess a boarder broader range of frequencies and nonlinear signal features could allow detection of heart sounds associated with heart failure earlier and direct the initiation of appropriate treatment. A signal from failing heart will likely be distorted. Nonlinearity could be a measure of such distortion. This could be also applied to other organs. A stethoscope with a broader frequency range could also potentially identify new frequencies in the development of heart failure and improve our understanding of the underlying pathophysiology of heart failure. Heart failure can be studied in a live pig model by tying off one of the coronary arteries causing ischemia or death to a portion of the heart muscle resulting in heart failure. This invention will allow heart sounds to be assessed in an animal model at baseline prior to tying off a coronary artery and then throughout the development of heart failure. This would provide better understanding of the pathophysiology of heart failure, its detection, and be a unique way to assess medical treatment of heart failure.

In addition to listening to heart sounds, stethoscopes are commonly used to listen to lung sounds. High frequency wheezing sounds from the lung can typically be heard with a stethoscope in patients with asthma as the respiratory airway constricts. By using the current disclosure to amplify the wheezing sounds and assessing a broader frequency range, both below and above the human hearing thresholds, will allow for earlier and more accurate diagnosis of asthma and other obstructive airway diseases like emphysema. This data can be combined with pulmonary function testing which can assess pulmonary obstruction as in asthma for a more accurate diagnosis and improve medical management of the patient. When the stethoscope is used to listen to the lungs it can with AI map out the location of the lung sounds in the respiratory cycle. This will result in a more accurate interpretation of the sounds. For example, wheezing at the end of forced expiration can be an early indicator of developing lung disease and wheezing throughout inspiration and expiration would indicate more severe airway disease. This additional information alone or in combination with other clinical data can result in a more accurate diagnosis and patient management. Thus, in one aspect, the current disclosure provides for recording the lung sound locations in the respiratory cycle and analyzing these with artificial intelligence and combining this with other clinical data for a more robust prognosis and evaluation of a patient.

It is not uncommon for a patient to have both heart and lung disease, so being able to assess both heart and lung sounds and analyzing those sounds with artificial intelligence and deep learning could significantly enhance the diagnosis by determining if a current symptom like shortness of breath is due to the heart disease or the lung disease or a combination of the two.

Recording heart and lung patterns while a patient is symptom free could also allow establishment of a personalized patient profile against which additional testing could be performed when the patient becomes symptomatic resulting in precise medical treatment (a precision medicine model).

Remote/Tele-health Applications

With the ability to transmit the sounds and graphic display and analysis of these body sounds, remote medical consultation (tele-health) would be greatly enhanced. This would create the opportunity to provide state-of-the-art consultation and healthcare in virtually any remote area of the world using this device and/or its accompanying characteristics of artificial intelligence analysis of multiple data points (ultrasound, pulmonary function test data, etc) and the design of a fixed sound receptor disk with offset margins and double-sided adhesion tape and external noise barrier.

All sound data with respect to the intensity of the sound, the frequency, the wave form, and its location in the cardiac cycle for this particular patient could be used as an indication of progression or regression of disease and provide a more precise approach to managing the patient's health (an example of precision medicine).

In a further embodiment, an array of detectors may be employed. In this embodiment, one collects sound signals simultaneously from disparate body locations to form a "sound image" of the area. This is a primary idea as visualization will likely help diagnostics. Thus, in one embodiment, multiple detectors may be placed on a body in various locations to collect sound from a patient's heart, stomach, joints (arms, knees, etc.) during exercise or other activity. This would help arrive at a diagnostic decision based on a combination of data from various locations. Further, as is a difference between low frequency sound propagation humans can hear and higher frequency vibrations of body elements (e.g. ribs with guide vibration propagation), which a human listener may not detect, both may be used for diagnostics.

In a further embodiment, a device and method to detect a broader range of body sounds than those capable of being detected via human hearing can be used alone or combined with other real-time or recorded clinical and analyzed with artificial intelligence to improve diagnostic accuracy and create learning opportunities for instructor directed and self-directed learning. The learner can interpret the data without the assistance of artificial intelligent then activate the artificial intelligence for comparison. Analysis of the differences can be provided to the learner as well as instructive feedback. The broader range of body sounds may be studied in combination with body sounds such as heart and lung with pulmonary function data and other clinical data for a more accurate diagnosis both within the normal range of hearing and outside the normal range of hearing.

Figure 4:
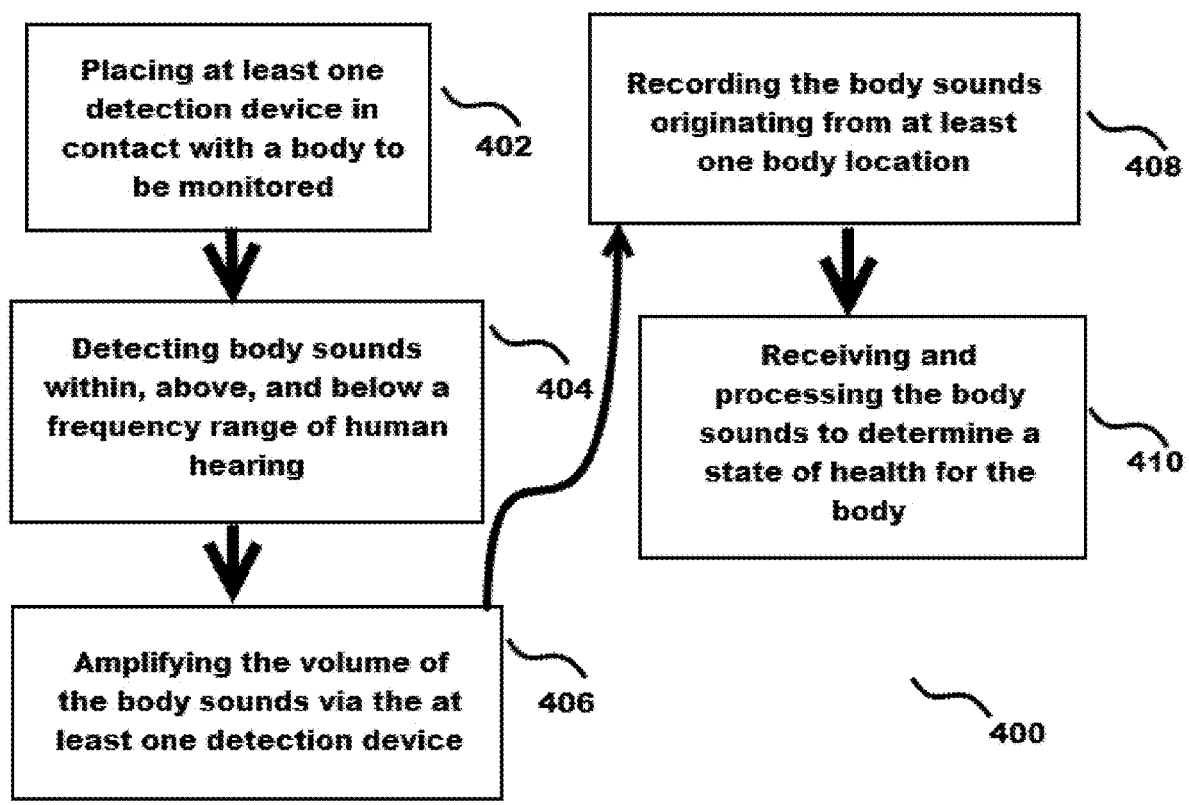
FIG. 4 shows a method of one embodiment of the current disclosure.

FIG. 4 shows a method 400 of one embodiment of the current disclosure. At step 402, at least one detection device is place in contact with a body being monitored. At step 404, body sounds within, above, and below the human range of hearing are detected. At step 406, the volume of the body sounds is amplified by the detection device. At step 408, the body sounds originating from the body location are recorded. At step 410, the body sounds are received and processed to determine a state of health for the body.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:
1. A method for monitoring and analyzing body sounds, the method comprising:
 placing at least one first detection device in contact with a body to be monitored;
 simultaneously detecting body sounds within, above and below a frequency range of human hearing;

assessing spatial distribution of sounds using an array of sensors in the at least one first detection device;

amplifying a volume of body sounds within, above and below a frequency range of human hearing and transmitting all of these simultaneously detected frequency ranges via the at least one first detection device;

recording the body sounds originating from at least one body location;

receiving and processing the body sounds by a hardware processor; and analyzing nonlinearity of the body sounds to determine a state of health of the body by the hardware processor.

2. The method of claim 1, further comprising forming a baseline sound recording for the body based on the body sounds recorded.

3. The method of claim 2, further comprising taking additional body sound recordings over time.

4. The method of claim 3, further comprising comparing the body sound recordings taken at different times to the baseline recording to determine differences in the body sound recordings.

5. The method of claim 1, further comprising analyzing at least one aspect of the body sounds including frequency, intensity, wave form, nonlinearity of waveform, or location of sound detected in a physiological cycle.

6. The method of claim 5, further comprising combining results from the analysis with other health data points of the body being monitored.

7. The method of claim 6, further comprising analyzing the combined results by deep learning and artificial intelligence.

8. The method of claim 1, wherein a second detection device is placed on the body being monitored at a location separate from the at least one first detection device.

9. A system for analyzing sounds generated by an animal's body, comprising:

at least one first detection device for simultaneous auscultation of internal sounds from the animal's body wherein the auscultated sounds are within, above and below human hearing range and transmitting all of these simultaneously detected frequency ranges, wherein the first detection device is in wireless communication with a receiver;

wherein the receiver receives the auscultated internal sounds from the first detection device;

a processor, in communication with the receiver, for generating audio and video output formed from the internal sounds auscultated by the first detection device;

a monitor for displaying the audio and video output from the processor; and further comprising wherein the processor is configured to analyze nonlinearity of the body sounds and associating same with a health status of the body.

10. The system of claim 9, wherein the processor communicates with at least one communication system other than the monitor.

11. The system of claim 9, wherein a peripheral margin is slightly offset from a middle portion of a surface of the first detection device.

12. The system of claim 11, wherein an adhesive is placed in the offset peripheral margin to affix a recording disk to the body surface to improve quality of recording of the body sounds and decrease external noise.

13. The system of claim 9, wherein the system forms a baseline sound recording for a body based on the body sounds recorded.

14. The system of claim 9, wherein the system analyzes at least one aspect of the body sounds such as frequency, intensity, wave form, nonlinearity of waveform, or location of sound detected in a physiological cycle.

15. The system of claim 9, wherein a second detection device is placed on the animal's body being monitored at a location separate from the at least one first detection device.

* * * * *